United States Patent [19]

Barnes et al.

[11] Patent Number: 4,505,819
[45] Date of Patent: Mar. 19, 1985

[54] METHOD FOR THE ANAEROBIC DEGRADATION OF ORGANIC MATERIAL

[75] Inventors: David Barnes, Caringbah; Peter J. Bliss, North Ryde, both of Australia

[73] Assignee: Unisearch Limited, Kensington, Australia

[21] Appl. No.: 513,525

[22] Filed: Jul. 13, 1983

Related U.S. Application Data

[63] Continuation of Ser. No. 293,078, Aug. 17, 1981, abandoned.

[30] Foreign Application Priority Data

Aug. 18, 1980 [AU] Australia .......................... PE5098/80

[51] Int. Cl.³ .............................................. C02F 3/28
[52] U.S. Cl. ..................................... 210/603; 210/610; 210/617; 48/197 A
[58] Field of Search ................................ 210/615–618, 210/603, 610, 903, 218, 197; 48/197 A; 435/167

[56] References Cited

U.S. PATENT DOCUMENTS

| | | | |
|---|---|---|---|
| 3,607,736 | 9/1971 | Yusho | 210/610 |
| 4,043,936 | 8/1977 | Francis et al. | 210/617 |
| 4,182,675 | 1/1980 | Jeris | 210/618 |
| 4,225,430 | 9/1980 | Bosman | 210/618 |
| 4,284,508 | 8/1981 | Jewell | 210/617 |
| 4,351,729 | 9/1982 | Witt | 210/603 |
| 4,352,738 | 10/1982 | Blay et al. | 210/617 |

FOREIGN PATENT DOCUMENTS 54-105850  8/1979  Japan .................................. 210/617

Primary Examiner—Benoit Castel
Attorney, Agent, or Firm—Millen & White

[57] ABSTRACT

A system for the anaerobic bacterial degradation of organic material in waste water, comprising introducing the waste water into a contact reactor, pumping the waste water into the bottom of a fluidized bed reactor containing anaerobic bacteria attached to the particles in the bed, the fluidized bed reactor having an effective volume not more than 0.35 times the effective volume of the contact reactor, returning the waste water which has passed through the fluidized bed reactor to the contact reactor and continuously or discontinuously removing treated effluent from the system.

A start-up procedure for the anaerobic treatment system is described comprising culturing anoxic bacteria in the system by adding nitrate ions to the waste water and gradually reducing the amount of nitrate ions in the stream until the population of anoxic bacteria is substantially replaced by a population of anaerobic bacteria. A viable microbial population is established in both the fluidized bed reactor and the contact reactor.

15 Claims, 1 Drawing Figure

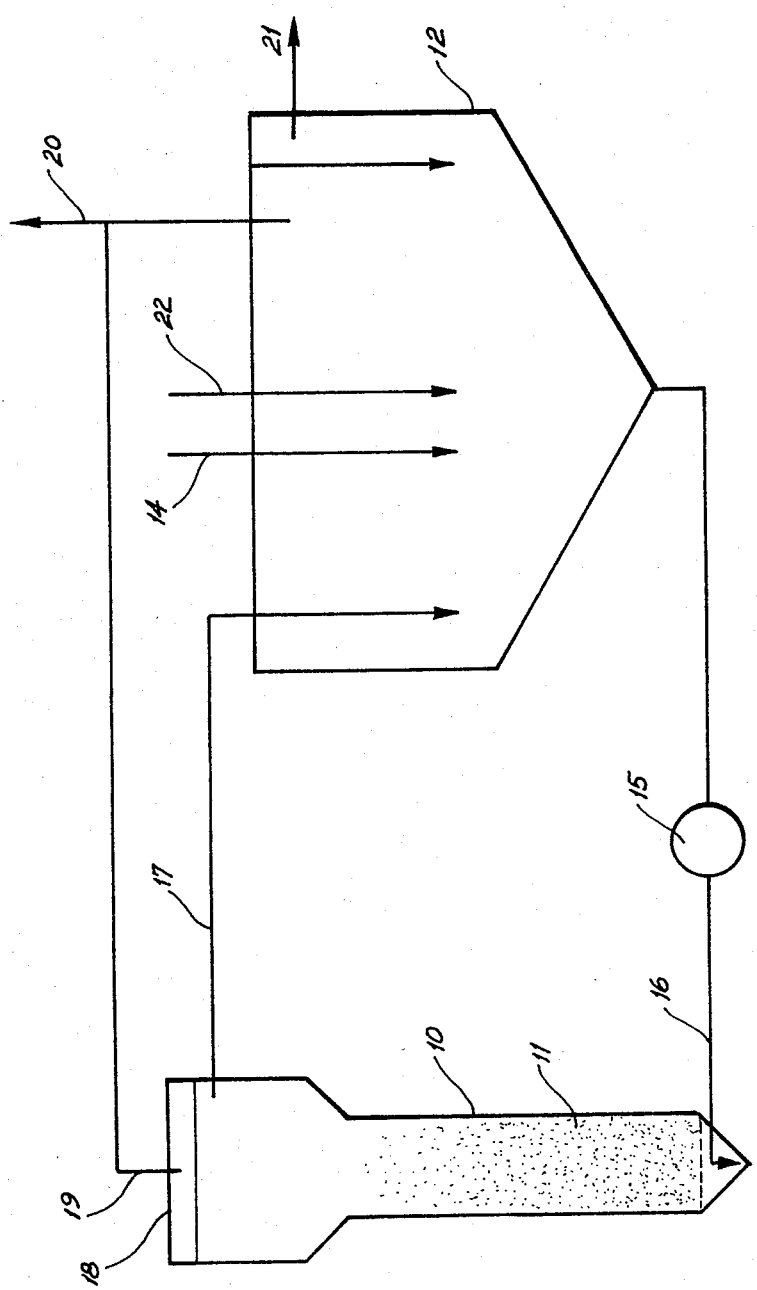

METHOD FOR THE ANAEROBIC DEGRADATION OF ORGANIC MATERIAL

This is a continuation of application Ser. No. 293,078 filed Aug. 17, 1981, now abandoned.

BACKGROUND OF THE INVENTION

The present invention relates to a method for the degradation of organic materials in a stream of an aqueous medium, such as trade waste, and a multiple vessel reactor system which includes a fluidized bed reactor and a contact reactor, for carrying out this process. The invention further resides in a method for establishing a population of anaerobic bacteria in a multiple vessel reactor system which includes a fluidized bed reactor and a contact reactor.

It is well known that bacterial degradation can remove organic materials from sewage, wastewater and other aqueous media. In an effort to improve the efficiency of such processes fluidized bed techniques have been used to culture aerobic bacteria. The aqueous medium to be treated is pumped upwardly into the bed to fluidized the media in the bed. The aerobic bacteria are grown in the bed and the treated water removed at the top of the column with some of the bed particles. These bed particles must then be cleaned to remove excess biomass generated by the growth of the bacteria and the cleaned particles returned to the column. The large amount of biomass generated in such a fluidized bed is a significant disadvantage in such a system as is the need to provide oxygen for the bacteria.

It has been proposed in U.S. Pat. No. 4,182,675 to remove biochemical oxygen demand (BOD) from waste water by forming a fluidized bed of microorganisms attached to a solid particulate carrier, continuously passing waste water to be treated through said fluidized bed, retaining the waste water in the fluidized bed for a sufficient period of time while controlling other necessary parameters and while maintaining the bed in an anaerobic condition to biologically convert substantially all of the biochemical oxygen demand to be removed from the waste water to methane gas, carbon dioxide and cellulose material. It is also disclosed that nitrified effluent may be added to the waste water and the mixture biologically converted to methane gas, carbon dioxide, nitrogen gas and cellulose material.

The process disclosed in U.S. Pat. No. 4,182,675 suffers from a number of difficulties from a practical point of view. The first of these is that it is difficult to get a population of anaerobic bacteria to remain adhered to the particulate carrier in the bed. Some time after start up there is a tendency for the bacterial layer on the substrate to slough off due to an apparent lack of any inherent capacity of the anaerobic bacteria to adhere to the particulate carrier. This loss of biomass substantially destroys the efficiency of the process. A further difficulty is that the process described does not work efficiently with trade wastes having high BOD concentration, i.e. BOD concentrations of more than 1,500 mg/l, typically more than 2,000 mg/l. In the process described if high BOD wastes are passed through fluidized beds of reasonable size slowly enough to provide residence times sufficient to bring about a substantial reduction of BOD then the bed will not remain fluidized. This latter problem is sought to be overcome in the above-mentioned specification by the use of plurality of fluidized beds in series. The present invention provides an alternative mode of overcoming this problem without the excessive cost of providing a plurality of fluidized beds in series.

A further difficulty with the process described in U.S. Pat. No. 4,182,675 is that it is not well adapted to handle changes in the BOD of the aqueous medium. In the prior art arrangement a substantial change in the BOD of the aqueous medium will lead to the degradation of the treated effluent due to the inability of the organisms in the bed to handle the increased BOD. The present invention seeks, by the use of two interconnected reaction tanks, to provide a system which can readily handle the rapid and substantial changes in BOD which occur in the practical handling of trade wastes.

SUMMARY OF THE INVENTION

The present invention consists in means for the anaerobic bacterial degradation of organic materials present in an aqueous medium, comprising a contact reactor, a fluidized bed reactor having an effective volume not more than 0.35 times the effective volume of the contact reactor, inlet means to introduce untreated aqueous medium into the contact reactor, pump means to pump aqueous medium from the contact reactor to the bottom of the fluidized bed reactor to fluidized the bed of a finely divided inert solid in the fluidized bed reactor, means to convey treated aqueous medium from the fluidized bed reactor to the contact reactor and an outlet for removing aqueous medium from the degradation means.

In a further aspect the present invention consists in a process for the anaerobic bacterial degradation of organic material present in an aqueous medium, comprising introducing the aqueous medium into a contact reactor pumping the aqueous medium into a fluidized bed reactor which has an effective volume not more than 0.35 times the effective volume of the contact reactor and which contains a bed of a finely divided inert solid which supports a population of substantially anaerobic bacteria, to maintain the bed of the fluidized bed reactor in a fluidized state, returning the aqueous medium which has passed through the fluidized bed reactor or a part thereof to the contact reactor and continuously or discontinuously withdrawing a treated effluent from the contact reactor or from the fluidized bed reactor.

The present invention still further consists in a method of establishing a population of substantially anaerobic bacteria in a multiple vessel reactor system which includes a fluidized bed reactor and a contact reactor, comprising passing a stream of an aqueous medium containing organic material and nitrate ions into the system to establish a population of substantially anoxic bacteria in the fluidized bed reactor and the contact reactor and gradually reducing the concentration of nitrate ions in the stream until the population of anoxic bacteria is substantially replaced by a population of anaerobic bacteria, the anaerobic microbial population being substantially fixed on the solid median of the fluidized bed reactor and is substantially free floating in the contact reactor.

DETAILED DISCUSSION OF THE INVENTION

Preferred embodiments of the process according to the present invention have been found to be particularly advantageous for the degradation of organic materials in a trade waste prior to sewer discharge. Conventional sewer discharge standards are between 300 and 600 mg/l of five day BOD (Biochemical oxygen demand) and suspended solids. For an anaerobic process the yield of biomass is very low, approximately 0.1–0.2 kg/kg BOD as opposed to 0.8–1.4 kg/kg BOD for a high rate aerobic process. Because of the low yield of biomass the anaerobic system can be optimized by appropriate adjustment of the flow and recycle rates to meet the pretreatment requirements for the majority of applications. For example, if a waste of 3000 mg/l BOD is reduced to a soluble BOD of 300 mg/l., a reduction of 90% which is obtainable in anaerobic processes, the yield of biological solids will be approximately 300 mg/l. Without separation of the biomass the total BOD and suspended solids in the effluent will meet the commonly applied sewer discharge standards of 600 mg/l of BOD and 600 mg/l of suspended solids. The integration of the anaerobic fluidized bed reactor and the anaerobic contact reactor with a minimum separation of biological solids will provide adequate pretreatment of many strong organic wastewaters.

The bed of the fluidized bed reactor may be made up of any finely divided inert and durable solid such as sand, crushed bricks, or anthracite. The particle size of the solid material will depend upon the rate of flow of the aqueous medium through the bed. The faster the flow the larger the particles will need to be if they are not to be washed out of the bed. Typically the inert solid particles will have a diameter of from 0.2 to 3 millimeters preferably 0.3 to 1.5 millimeters. They are preferably all of substantially uniform size. The particles need not be of a strictly spherical shape and the above reference to diameter should be read in that light.

The multiple vessel reactor system is preferably initially seeded by pumping through the system an aqueous medium of the type which is to be treated to which has been added an amount of nitrate ions in some suitable form and preferably in an amount of 25 to 500 mg/l as nitrate nitrogen, more preferably 40 to 100 mg/l. The amount of nitrate is preferably at no time greater than the stochiometric amount of BOD present in the aqueous media. Naturally occurring anoxic bacteria, i.e. those that extract their oxygen requirement from nitrate ions, will populate the system and are able to adhere to the bed particles in the fluidized bed reactor to prevent themselves being swept out of the fluidized bed reactor. As the anoxic bacterial population grows it is preferrable to reduce the rate of flow of the aqueous medium through the fluidized bed reactor. The particles grow in size with the development of a bacterial coating which effectively reduces the density of the particles. It may be desirable to withdraw some of the inert solid particles from the fluidized bed reactor as the bed height grows due to the reduction in particle density as the bacterial coating increases. A similar microbial population is established in the contact reactor but as this reaction does not contain substantial amounts of the solid support media the microorganisms are in a suspended growth form.

Once a suitable population of anoxic bacteria has been established in the system the nitrate ion concentration is reduced which causes the population of anoxic bacteria to be reduced and allows the growth of anaerobic bacteria. It is preferred that the system be seeded with a source of anaerobic bacteria such as digested sludge from a sewage works, as the nitrate ion content of the aqueous medium is reduced. It is preferable that the BOD of the aqueous media be increased as the nitrate ion is decreased. Thus, for example, an initial BOD of 600 mg/l and a nitrate ion concentration of 100 mg/l as nitrate nitrogen may be changed until a substantially steady state is achieved in which the BOD has been increased to the level of the waste to be treated which could be typically between 3,000 and 50,000 mg/l and the nitrate ion concentration has been reduced to a minimum of say 1 to 40 mg/l.

It has been found difficult to get anaerobic bacteria to attach onto the particles in the fluidized bed reactor if the particles have not previously been conditioned by the growth of the anoxic bacteria.

It is desirable that, once a population of substantially anaerobic bacteria is established in the system, a small quantity of nitrate ion continues to be added to the aqueous media. Amounts of nitrate as low as 1 mg/l, but preferably 20 to 40 mg/l, as nitrate nitrogen, have been found advantageous to maintain the stability of the fluidized bed reactor and to assist in the reestablishment of a coating of anaerobic bacteria on the solid particle if there is an excessive loss of biomass.

The nitrate ion is preferably added to the aqueous media as the solid salt or as a concentrated solution. It is not usually desirable to add the nitrate ion in the form of a nitrified effluent as this would unnecessarily reduce the concentration of BOD in the aqueous media, which would carry an economic penalty.

With time there is a tendency for biomass to build up in thickness around the individual particles of the bed. This results in a reduction in the density of the biomass—coated particles and, therefore, in a tendency for such particles to migrate upwardly in the fluidized bed reactor and even, if appropriate precautions are not taken, to carry over excessive amount of particulate material into the contact reactor. Limiting the biomass thickness on the particles promotes maximum activity of the biomass and is required to prevent carry over of solid particles in the flow from the fluidized bed reactor. This control is preferably achieved solely by adjusting the upflow rate of the media through the fluidized bed reactor. For silica sand of 0.3 to 0.6 mm size, for example, flow rates of 3 to $10 \cdot m^{-2} s^{-1}$ have been found suitable when treating a mixed waste of molasses and yeast extract. Retention of the particles in the fluidized bed reactor is enhanced by providing in the reactor a section at the top of the reactor, above the normal surface level of the fluidized bed, which has an enlarged cross sectional area. The height of this enlarged cross sectional area preferably does not exceed 35% of the total fluidized bed reactor height, the upper section of the reactor contains little of the solid support median in its simplest form the upper section of the reactor has a cross sectional area between 1.2 and 8 times the area of the lower section of the reactor. The upper section can be designed to any geometry suitable for retaining the biomass and solids in the fluidized bed reactor. The upper section can be concentrically or excentrically sited relative to the lower section of the reactor. The upper section can contain interceptor devices such as plates to facilitate the maintainance of a stable depth of fluidized bed. Thus any clarification takes place essentially in the fluidized bed reactor.

The recyling of media having high BOD concentrations between the contact reactor and the fluidized bed reactor is essential to enable flow rates through the fluidized bed reactor to be obtained which are sufficiently high to achieve fluidization of the bed and control the thickness of the biomass on the particles in the fluidized bed reactor. In addition multiple passage of the aqueous medium through the system by recirculation enhances the total removal efficiency as compared with a single fluidized bed reactor. This is thought to be due to the integration of the biological reactions in the fluidized bed reactor and the contact reactor.

The anaerobic bacteria, once established in the system, can produce, under appropriate conditions, methane by the degradation of the organic content of the aqueous medium. Methane is liberated from both the fluidized bed reactor and the content reactor. This may be used as an energy source for running the process. The contact reactor and the fluidized bed reactor and the ancillary systems are preferably run as a closed system to preserve the anaerobic conditions in the system and to capture any methane produced. This also prevents the emission of unpleasant odors from the system. If methane is to be produced the conditions in the system should be controlled to optimum conditions for methane production. The principal requirement appears to be a temperature between 32° and 38° C. If methane is not produced the degradation of the organic material will proceed only to the stage of conversion to simpler compounds such as organic acids.

The fluidized bed reactor preferably has an effective volume 0.2 to 0.02 times the effective volume of the contact reactor. The contact reactor preferably includes inlet means for untreated aqueous medium and for a source of nitrate ions, either as a solid or a concentrated solution although the nitrate nitrogen could be added anywhere in the system. The pump preferably pumps the aqueous medium to the base of the fluidized bed reactor which is constructed as a fluidised bed column. The medium which has passed through the fluidized bed reactor is preferably collected at the top of the reactor and returned through a return line to the contact reactor. If desired the returning material may be injected into the contact reactor in a manner which will bring about mixing of the contents of that reactor and enhance biological action in that reactor. In another embodiment stirring means may be provided in the contact reactor.

In any bacterial process excess biomass will to some extent to created. In the product system this excess biomass will float free from the particles in the fluidized bed reactor due to the flow rate of the aqueous medium, as has been described above, and will carry over into the contact reactor. The process of degradation will therefore proceed in simultaneously in both reactors. As would be expected the reaction will continue more rapidly in the fluidized bed reactor, however the reaction taking place in the contact reactor contributes significantly to the efficiency of the present process. Excess biomass from the reactors will eventually pass out with the treated effluent.

BRIEF DESCRIPTION OF THE DRAWINGS

Hereinafter given by way of example only is a preferred embodiment of this invention described with reference to the accompanying drawing diagramatically illustrating a pilot scale apparatus for carrying out the process according to this invention.

DISCUSSION OF THE APPARATUS

The apparatus includes a fluidised bed reactor 10 containing a bed of sand 11, and a contact reactor 12. The contact reactor 12 receives an aqueous stream of trade waste through line 14. The waste stream is then pumped from the contact reactor 12 through pump 15 to the lower end of the fluidized bed reactor 10 through line 16.

The fluidized bed reactor 10 contains graded sand constituting the bed 11 which reaches up about ¾ of the effective height of the reactor. Waste water pumped into the reactor 10 fluidizes the bed 11 and is then returned to contact reactor 12 through line 17. The waste water can be recycled through the system if desired. A proportion of the output from the system is discharged into a conventional sewer through line 21. This flow pattern is described only as an illustration, the system should be considered as a whole.

The upper end of the fluidized bed reactor 10 is provided with a cap 18 which collects methane generated in the fluidized bed reactor 10 and vents it through line 19 into gas outlet line 20 exiting from its contact reactor 12.

The fluidized bed reactor 10 has a volume of approximately 0.03 cubic meters and the contact reactor 12 has a volume of 0.22 cubic meters. A concentrated solution of sodium nitrate is metered into the contact reactor 12 through line 22.

The above described apparatus was used to study the anaerobic degradation of a synthetic waste water formed from yeast extract and molasses.

The initial feed stream had a BOD of 300 mg/l and from 80 to 100 mg/l of nitrogen as nitrate. The system was needed with settled sewage and the feed stream continuously recycled between the fluidized bed reactor and the contact reactor.

Once signs of biomass growth appeared on the sand in the fluidized bed reactor the system was run with 170 hour hydraulic retention time. The BOD of the feed stream was gradually increased incrementally at each of the batch feeding steps to about 2000 mg/l and the nitrate concentration reduced to 50 mg/l nitrogen as nitrate. This change took place over a period of one month.

In this process a change of color was observed in the organisms in the system from an initial grey/brown color of the population of anoxic bacteria to a block color of the population of anaerobic bacteria formed as the BOD was increased and the nitrate concentration reduced.

The nitrate ion concentration was thereafter reduced gradually so as to avoid vigorous gassing which may occur if too much nitrate nitrogen is present. A steady state nitrate concentration of about 20 mg/l was found satisfactory.

As the nitrate ion concentration was reduced the hydraulic retention time was reduced to 48 hours. The temperature was controlled at 35° C.±3° C. to promote methane generation, the flow rate was 4 l·m$^{-2}$ sec$^{-1}$, and the pH 6.89. The following results were obtained from the anaerobic reactor system.

TABLE I

| Week No. | BOD$_5$ mg/l | | | Treatment Efficiency % Unfiltered/Filtered |
|---|---|---|---|---|
| | Raw Feed | Unfiltered Effluent | Filtered Effluent | |
| 1 | 560 | 260 | — | 54/— |
| 3 | 660 | 230 | 140 | 65/79 |
| 5 | 1840 | 240 | 170 | 87/91 |
| 8 | 2300 | 600 | 330 | 74/86 |
| 9 | 2280 | 470 | 180 | 79/92 |
| 10 | 2280 | 320 | 180 | 86/92 |

TABLE I-continued

| Week No. | Raw Feed | BOD₅ mg/l Unfiltered Effluent | Filtered Effluent | Treatment Efficiency % Unfiltered/Filtered |
|---|---|---|---|---|
| 11 | 2300 | 280 | 180 | 88/92 |

Visual observation suggested that the gas flame was approximately 1 l/min and the gas burnt with the pale blue flame characteristic of methane.

We claim:

1. In a process for the anaerobic bacterial degradation of organic material present in an aqueous medium waste stream comprising introducing the influent waste stream into a system comprised of a holding tank and a fluidized bed anaerobic reactor, recycling at least in part the waste stream between the fluidized bed and the holding tank to anaerobically degrade organic material present in the waste stream in the fluidized bed, and discharging treated effluent from the system, the improvement comprising:

introducing a high strength aqueous medium waste stream having a BOD concentration of at least 1,500 mg/l first into a holding tank of sufficient size and having a sufficient population of anaerobic bacteria therein to conduct degradation of organic components in the influent waste stream whereby said holding tank functions as a contact reactor under anaerobic conditions;

pumping the aqueous medium waste stream from the contact reactor into a fluidized bed reactor maintained under anaerobic conditions, having an effective volume not more than 0.35 times the effective volume of the contact reactor and containing a bed of finely divided inert solid supporting a population of substantially anaerobic bacteria, at a rate effective to maintain the bed in a fluidized state and to also conduct degradation of organic components in the waste stream;

treating the aqueous medium waste stream in said contact reactor and fluidized bed reactor under temperature conditions and for a residence time sufficient to generate methane, both in said contact reactor and said fluidized bed reactor;

returning at least a part of the aqueous medium waste stream, which has passed through the fluidized bed reactor, to the contact reactor at a rate effective to achieve multiple passage of the aqueous medium through the contact reactor and the fluidized bed reactor; and withdrawing a treated effluent stream from at least one of the fluidized bed reactor and the contact reactor whereby higher purification levels can be attained than when conducting purification in a fluidized bed reactor connected to a holding tank.

2. A process as in claim 1 wherein said aqueous medium contains nitrate ions in a concentration of from 1–40 mg/l of nitrate nitrogen.

3. A process as in claim 2 wherein said concentration of nitrate nitrogen is 20–40 mg/l.

4. A process as in claim 2 wherein said concentration of nitrate nitrogen is maintained by adding a sufficient quantity of nitrate ion to the aqueous media to maintain reaction stability in the fluidized bed reactor and to enhance reestablishment of anaerobic bacteria population supported upon loss of effective biomass.

5. A process as in claim 4 wherein said concentration of nitrate nitrogen is 20–40 mg/l.

6. A process as in claim 4 further comprising adding said nitrate ion in the form of a solid salt.

7. A process as in claim 4 further comprising adding said nitrate ion in the form of a concentrated solution.

8. A process as in claim 1 wherein said aqueous medium is pumped through said fluidized bed at a rate of $3-10$ $l \cdot m^{-2} sec^{-1}$.

9. A process as in claim 1 wherein said contact reactor and said fluidized bed reactor are maintained at a temperature of 32°–38° C.

10. A process as in claim 9 wherein the thus-generated methane is vented.

11. A process as in claim 10 wherein the BOD level in the influent waste stream is 3,000–50,000 mg/l.

12. A process as in claim 1 wherein said fluidized bed reactor has an effective volume of 0.2–0.02 times the effective volume of said contact reactor.

13. A process as in claim 1 wherein said anaerobic bacterial degradation is conducted in a closed system to maintain anaerobic conditions in the system and to capture the methane produced.

14. A process as in claim 1 further comprising employing said contact reactor as a surge buffer tank for high concentration and quantities of wastewater to thereby avoid poisoning said fluidized bed reactor.

15. A process as in claim 1 wherein the BOD level in the influent waste stream is more than 2,000 mg/l.

* * * * *